(12) United States Patent
Bloch

(10) Patent No.: US 12,027,059 B1
(45) Date of Patent: Jul. 2, 2024

(54) SYSTEMS AND METHODS FOR CORRECTING DYSLEXIA AND OTHER READING DEFICIENCIES

(71) Applicant: Reading Without Limits, Inc., Carlsbad, CA (US)

(72) Inventor: David Alexander Bloch, Carlsbad, CA (US)

(*) Notice: Subject to any disclaimer, the term of this patent is extended or adjusted under 35 U.S.C. 154(b) by 153 days.

(21) Appl. No.: 17/525,906

(22) Filed: Nov. 14, 2021

Related U.S. Application Data

(60) Provisional application No. 63/113,825, filed on Nov. 13, 2020.

(51) Int. Cl.
*G09B 17/00* (2006.01)
*G06V 20/40* (2022.01)
*G10L 15/22* (2006.01)
*G10L 25/51* (2013.01)
*G16H 20/70* (2018.01)
*G16H 40/67* (2018.01)
*G16H 50/20* (2018.01)

(52) U.S. Cl.
CPC ........... *G09B 17/003* (2013.01); *G06V 20/40* (2022.01); *G10L 15/22* (2013.01); *G10L 25/51* (2013.01); *G16H 20/70* (2018.01); *G16H 40/67* (2018.01); *G16H 50/20* (2018.01)

(58) Field of Classification Search
CPC ...... G09B 17/00; G09B 17/003; G16H 40/67; G16H 20/70; G16H 50/20; G06V 20/40; G10L 5/22; G10L 25/51
See application file for complete search history.

(56) References Cited

U.S. PATENT DOCUMENTS

| | | | |
|---|---|---|---|
| 6,685,477 B1* | 2/2004 | Goldman | G09B 1/36 434/178 |
| 2002/0119429 A1* | 8/2002 | Barton | G09B 17/003 434/178 |
| 2021/0375480 A1* | 12/2021 | Mahon | G06N 20/00 |

* cited by examiner

*Primary Examiner* — Timothy A Musselman
(74) *Attorney, Agent, or Firm* — Michael D. Eisenberg

(57) ABSTRACT

An example operation may include one or more of sending a plurality of anchor words to a user device to be displayed on a user interface of the dyslexia treatment application; providing at least one prompt to the user of the dyslexia treatment application to create tiles based on the plurality of the anchor words; responsive to receiving the tiles and associated responses from the user of the dyslexia treatment application, analyzing the tiles and the associated responses; and generating a score based on analysis of the tiles and the associated responses.

18 Claims, 18 Drawing Sheets

| C1 | C2 | C3 | C4 | C5 | C6 | C7 | C8 | C9 | C10 |
|----|----|----|----|----|----|----|----|----|-----|
| ab | eb | ib | ob | ub | abe | ebe | ibe | obe | ube |
| ac | ec | ic | oc | uc | ace | ece | ice | oce | uce |
| ad | ed | id | od | ud | ade | ede | ide | ode | ude |
| af | ef | if | of | uf | afe | efe | ife | ofe | ufe |
| ag | eg | ig | og | ug | age | ege | ige | oge | uge |
| ah | eh | ih | oh | uh | ahe | ehe | ihe | ohe | uhe |
| aj | ej | ij | oj | uj | aje | eje | ije | oje | uje |
| ak | ek | ik | ok | uk | ake | eke | ike | oke | uke |
| al | el | il | ol | ul | ale | ele | ile | ole | ule |
| am | em | im | om | um | ame | eme | ime | ome | ume |
| an | en | in | on | un | ane | ene | ine | one | une |
| ap | ep | ip | op | up | ape | epe | ipe | ope | upe |
| ar | er | ir | or | ur | are | ere | ire | ore | ure |
| as | es | is | os | us | ase | ese | ise | ose | use |
| at | et | it | ot | ut | ate | ete | ite | ote | ute |
| av | ev | iv | ov | uv | ave | eve | ive | ove | uve |
| aw | ew | iw | ow | uw | awe | ewe | iwe | owe | uwe |
| ax | ex | ix | ox | ux | axe | exe | ixe | oxe | uxe |
| ay | ey | iy | oy | uy | aye | eye | iye | oye | uye |
| az | ez | iz | oz | uz | aze | eze | ize | oze | uze |

FIG. 3A

|       |     |     |     |     |     |     |     |     |     |     |     |     |     |     |     |     |     |     |     |     |     |     |     |     |
|-------|-----|-----|-----|-----|-----|-----|-----|-----|-----|-----|-----|-----|-----|-----|-----|-----|-----|-----|-----|-----|-----|-----|-----|-----|
|       |     |     |     |     |     |     |     |     |     |     |     |     |     |     |     |     |     |     |     |     | ant | ent | int | ont | unt |
|       |     |     |     |     |     |     |     |     |     |     |     |     |     |     |     |     |     | ang | eng | ing | ong | ung |     |     |     |
|       |     |     |     |     |     |     |     |     |     |     |     |     |     |     |     |     |     |     |     |     |     |     |     |     |
|       |     |     |     |     | aff | eff | iff | off | uff |     |     |     |     |     |     |     |     |     |     |     |     |     |     |     |     |
|       |     |     |     |     | agg | egg | igg | ogg | ugg |     |     |     |     |     |     |     |     |     |     |     |     |     |     |     |     |
|       |     |     |     |     |     |     |     |     |     |     |     |     | ack | eck | ick | ock | uck |     |     |     |     |     |     |     |     |
|       |     |     |     |     |     |     |     |     |     |     |     |     | all | ell | ill | oll | ull |     |     |     |     |     |     |     |     |
|       |     |     |     |     |     |     |     |     |     |     |     |     | and | end | ind | ond | und |     |     |     |     |     |     |     |     |
|       |     |     |     |     |     |     |     |     |     |     |     |     |     |     |     |     |     | ass | ess | iss | oss | uss |     |     |     |
|       |     |     |     |     |     |     |     |     |     |     |     |     |     |     |     |     |     | ast | est | ist | ost | ust |     |     |     |
|       |     |     |     |     |     |     |     |     |     |     |     |     |     |     |     |     |     |     |     |     |     |     |     |     |     |
|       |     |     |     |     |     |     |     |     |     |     |     |     | azz | ezz | izz | ozz | uzz |     |     |     |     |     |     |     |     |
| ab | eb | ib | ob | ub |
| ac | ec | ic | oc | uc |
| ad | ed | id | od | ud |
| af | ef | if | of | uf |
| ag | eg | ig | og | ug |
| ah | eh | ih | oh | uh |
| aj | ej | ij | oj | uj |
| ak | ek | ik | ok | uk |
| al | el | il | ol | ul |
| am | em | im | om | um |
| an | en | in | on | un |
| ap | ep | ip | op | up |
| ar | er | ir | or | ur |
| as | es | is | os | us |
| at | et | it | ot | ut |
| av | ev | iv | ov | uv |
| aw | ew | iw | ow | uw |
| ax | ex | ix | ox | ux |
| ay | ey | iy | oy | uy |
| az | ez | iz | oz | uz |

FIG. 3B

| bu | cu | du | fu | gu | hu | ju | ku | lu | mu | nu | pu | ru | su | tu | vu | wu | xu | yu | zu | pru |
| bo | co | do | fo | go | ho | jo | ko | lo | mo | no | po | ro | so | to | vo | wo | xo | yo | zo | pro |
| bi | ci | di | fi | gi | hi | ji | ki | li | mi | ni | pi | ri | si | ti | vi | wi | xi | yi | zi | pri |
| be | ce | de | fe | ge | he | je | ke | le | me | ne | pe | re | se | te | ve | we | xe | ye | ze | pre |
| ba | ca | da | fa | ga | ha | ja | ka | la | ma | na | pa | ra | sa | ta | va | wa | xa | ya | za | pra |

|   |    |    |    |    |    |    |    |    |    |    |    |    | st | str |
|---|----|----|----|----|----|----|----|----|----|----|----|----|----|-----|
|   |    |    |    |    |    |    |    |    |    |    |    | sp | squ |     |
|   |    |    |    |    |    |    |    |    |    |    | sn | spr |    |     |
|   |    |    |    |    |    |    |    |    |    | sm | spl | thr |   |     |
|   | cy |    |    | gu |    | py | si | sch | ty |   |   | y |   | aught |
| by | cr |    | gh |    | ph | sk | scr | tw |   | s | ight | tion | tial | ought | ge |
| bl | ct | dy | fr | gr | kr | pl | sh | sy | th | wh |  | es | ing | sion | sial | ough | tle |
| br | ch | dr | fl | gl | kl | my | ny | pr | qu | sc | sw | tr | wr | able | ed | iste | cion | cial | ous | ly |

FIG. 3C

| | | | | | | | | | |
|---|---|---|---|---|---|---|---|---|---|
| it / sit | us / bus | or / for | an / can | ay / day | ot / hot | est / best | ur / fur | ap / tap | oy / toy |
| ut / nut | ust / must | ar / car | ep / step | ow / cow | as / last | es / yes | er / her | ip / lip | ew / new |
| et / pet | is / his | ir / bird | op / hop | at / sat | ing / king | im / him | ell / fell | ock / lock | ad / bad |
| un / sun | am / ham | all / ball | ick / sick | up / cup | on / pond | ent / went | um / gum | ig / big | ud / mud |
| in / win | ong / song | ack / back | ug / hug | id / lid | en / pen | om / mom | ill / will | ag / bag | ed / bed |
| ace / face | uge / huge | ame / name | ore / more | ave / gave | ice / dice | ake / make | ime / time | ere / here | ose / nose |
| ade / made | ike / bike | ine / line | ape / grape | ate / late | ide / wide | oke / joke | ile / smile | ipe / wipe | ite / kite |
| ife / life | age / cage | ule / rule | ire / tire | ote / note | ive / give | ize / size | tion / action | able / table | light / night |
| ea / read | oa / road | ee / feel | oe / toe | ai / tail | au / haul | ou / out | oi / oil | ue / glue | ie / tie |
| ch / chick | th / that | bl / block | st / stop | sm / small | qu / quick | pl / place | gr / grade | thr / throw | spr / spring |

FIG. 3D

POWER E MATRIX

| ab_ | ac_ | ad_ | af_ | ag_ |
|-----|-----|-----|-----|-----|
| ah_ | aj_ | ak_ | al_ | am_ |
| an_ | ap_ | ar_ | as_ | at_ |
| av_ | aw_ | ax_ | ay_ | az_ |

FIG. 4B

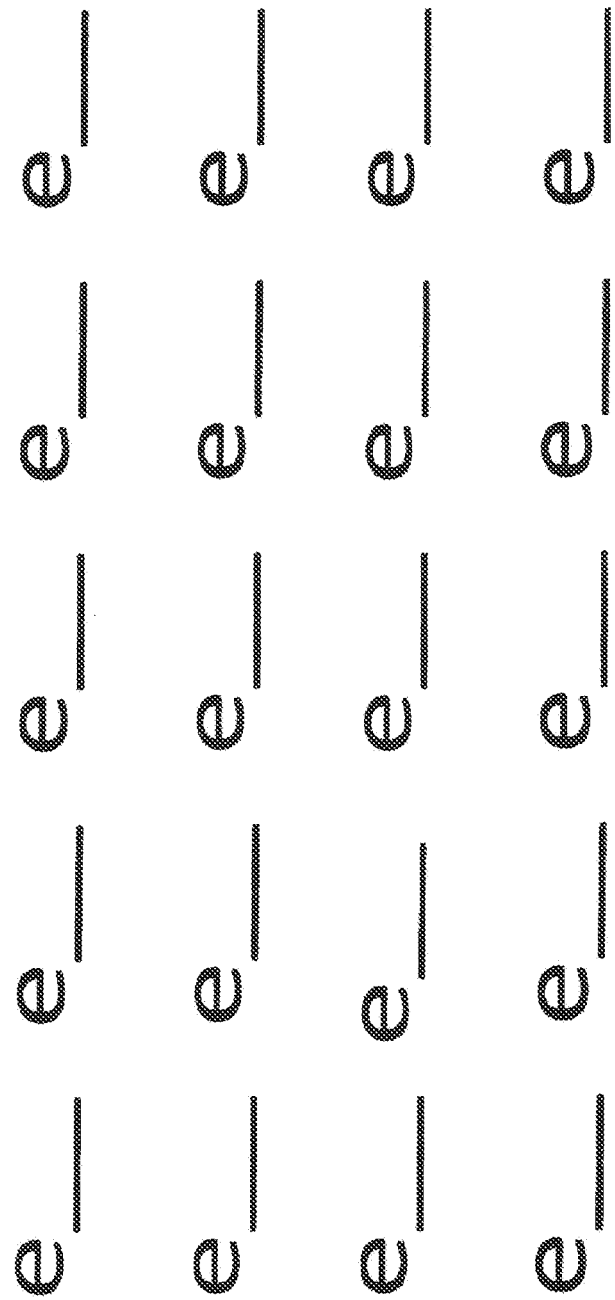

POWER E MATRIX eb_ ec_ ed_ ef_ eg_
eh_ ej_ ek_ el_ em_
en_ ep_ er_ es_ et_
ev_ ew_ ex_ ey_ ez_

FIG. 4D

POWER E MATRIX

| ib_ | ic_ | id_ | if_ | ig_ |
|------|------|------|------|------|
| ih_ | ij_ | ik_ | il_ | im_ |
| in_ | ip_ | ir_ | is_ | it_ |
| iv_ | iw_ | ix_ | iy_ | iz_ |

FIG. 4F

POWER E MATRIX

| ob_ | oc_ | od_ | of_ | og_ |
| oh_ | oj_ | ok_ | ol_ | om_ |
| on_ | op_ | or_ | os_ | ot_ |
| ov_ | ow_ | ox_ | oy_ | oz_ |

FIG. 4H

MATRIX U

FIG. 4I

POWER E MATRIX

| ub_ | uc_ | ud_ | uf_ | ug_ |
| uh_ | uj_ | uk_ | ul_ | um_ |
| un_ | up_ | ur_ | us_ | ut_ |
| uv_ | uw_ | ux_ | uy_ | uz_ |

FIG. 4J

| | |
|---|---|
| whole word | investigate |
| anchors pulled | in es ig ate (short short short long ) |
| adding lead letters | in ves tig ate |
| say parts and sequence | ate |
| | tigate |
| | vestigate |
| | investigate |

| | |
|---|---|
| whole word | pandemonium |
| anchors pulled | an em on iu (short short short double) |
| add lead letters | pan dem on ium |
| say parts and sequence | ium |
| | monium |
| | demonium |
| | pandemonium |

| | |
|---|---|
| whole word | unconsciously |
| anchors pulled | un on cious ly (short short ending ending) |
| add lead letters | un con scious ly |
| say part and sequence | ly |
| | sciously |
| | consciously |
| | unconsciously |

FIG. 5

SYSTEMS AND METHODS FOR CORRECTING DYSLEXIA AND OTHER READING DEFICIENCIES

CROSS-REFERENCES TO RELATED APPLICATIONS

This application claims priority from U.S. Provisional Application Ser. No. 63/113,825 filed Nov. 13, 2020, which is hereby incorporated herein by reference in the respective in its entirety.

BACKGROUND OF THE INVENTION

Up to 30% of the population has a reading disability of some sort and up to 15% have dyslexia Dyslexia is the number one learning disability in the USA. The underlying mechanism of dyslexia has been elusive. Thus, a cure and correction for dyslexia is still being researched by the medical community. Current methods of remediation for dyslexia are mediocre at best, which often take years to achieve substantial improvement.

The traditional method of teaching reading involves either a phonics based approach (sound pattern) or sight reading (whole word/memorization approach). Individuals with dyslexia are unable to learn reading in this manner. In fact, by definition students with dyslexia cannot learn to read using a phonics-based approach (i.e., dysphonesia). However, methods of correction for dyslexia still try to use phonics to teach them to read. The mostly widely accepted method of correction for dyslexia is teaching a person with dyslexia via the Orton-Gillingham method. The Orton-Gillingham method is reported to be extremely time intensive process that needs to be administered by a highly experienced educator. Some independent evaluators of Orton-Gillingham method claim that is not all that effective.

What is needed is a reliable and facile method of correction for dyslexia.

SUMMARY

One example embodiment provides a processor and memory of an ad processing server, wherein the processor is configured to: send a plurality of anchor words to a user device to be displayed on a user interface of the dyslexia treatment application; provide at least one prompt to the user of the dyslexia treatment application to create tiles based on the plurality of the anchor words; responsive to receiving the tiles and associated responses from the user of the dyslexia treatment application, analyze the tiles and the associated responses; and generate a score based on analysis of the tiles and the associated responses.

Another example embodiment provides a method that includes one or more of sending a plurality of anchor words to a user device to be displayed on a user interface of the dyslexia treatment application; providing at least one prompt to the user of the dyslexia treatment application to create tiles based on the plurality of the anchor words; responsive to receiving the tiles and associated responses from the user of the dyslexia treatment application, analyzing the tiles and the associated responses; and generating a score based on analysis of the tiles and the associated responses.

A further example embodiment provides a non-transitory computer readable medium comprising instructions, that when read by a processor, cause the processor to perform one or more of sending a plurality of anchor words to a user device to be displayed on a user interface of the dyslexia treatment application; providing at least one prompt to the user of the dyslexia treatment application to create tiles based on the plurality of the anchor words; responsive to receiving the tiles and associated responses from the user of the dyslexia treatment application, analyzing the tiles and the associated responses; and generating a score based on analysis of the tiles and the associated responses.

In another embodiment, a method for treating dyslexia comprises: providing, by a doctor, a plurality of anchor words to a dyslexia patient; prompting, by the doctor, the dyslexia patient to create tiles based on the plurality of anchor words; analyzing, by the doctor, the tiles and associated responses provided by the dyslexia patient; and calculating a score based on analysis of the tiles and the associated responses.

BRIEF DESCRIPTION OF DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

FIG. 3A-3D are depictions of the anchor matrices.

FIG. 4A-4K are depictions of various letter and power letter matrices.

FIG. 5 is a depiction of an example of an implementation of the invention.

Figure 1:
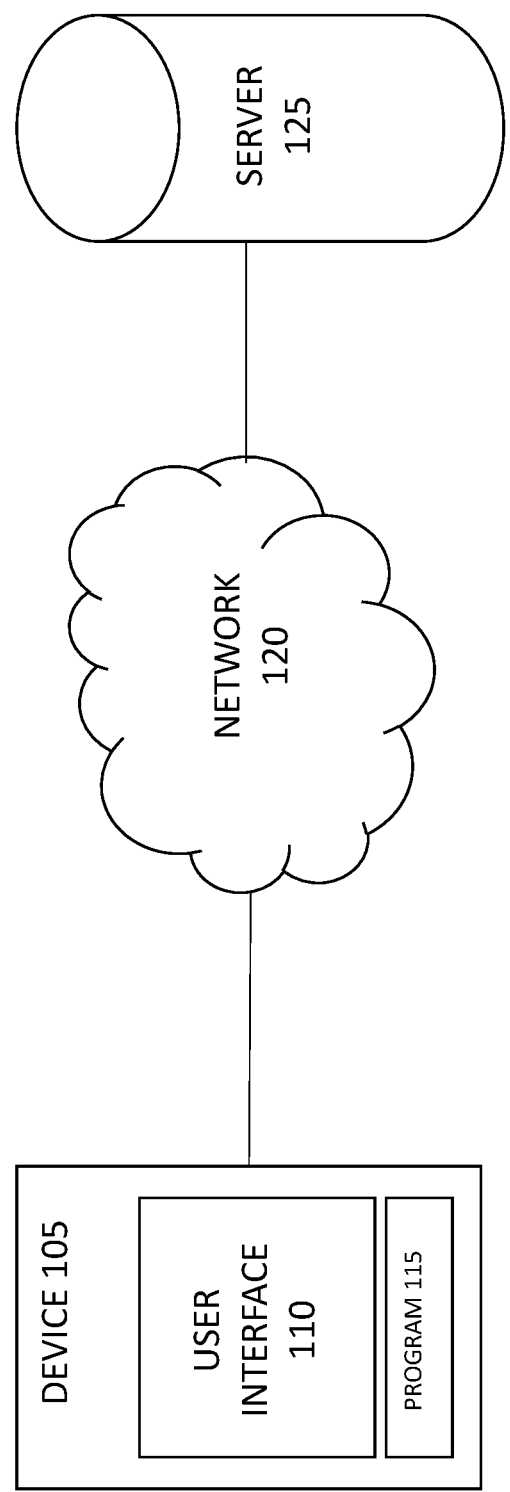
FIG. 1 is a depiction of a computing environment for dyslexia and correcting reading deficiencies.

The various embodiments of the present invention will hereinafter be described in conjunction with the appended drawings.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Reference is also made to the figures, as presented herein. The figures are not intended to be exhaustive or to limit the invention to the precise form disclosed. It should be understood that the invention can be practiced with modification and alteration, and that the invention be limited only by the claims and the equivalents thereof.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

The systems and methods herein are directed to individuals with dyslexia and other reading deficiencies, such as reading disabilities and dyslexia and individuals who have not learned to read with traditional methods. More specifically, the systems and methods herein correct dyslexia and other reading deficiencies, treat without emphasizing phonics, sight reading, picture books, or verbal cues. The systems and methods herein can be implemented in: (1) electronic or digitized form via a computing environment; (2) in hard copy form via training booklets, flashed cards, or printed media; or (3) a combination of (1) and (2). The mechanism behind the systems and methods herein is the reprogramming of visual and neuro-cognitive processing in the brain through a series of visual drills. Some of the drills can be considered vision therapy and some of the drills are reading therapy. Combined the drills can be considered "visual cross training", which break "bad brain habits" and thus allowing poor readers to read proficiently. The diagnosis and treatment, as implemented in: (1) electronic or digitized form via a computing environment; (2) in hard copy form via training booklets, or (3) a combination of (1) and (2), should be performed in full by a professional trained in eye care or in part with a reading professional working in conjunction with a professional trained in eye care.

The correction process is based on retraining visual and cognitive processing in the brain. Individuals with dyslexia and other reading deficiencies are in the habit of incorrectly storing and retrieving key visual and auditory information pertaining to reading. Through a series of special drills and tools, as disclosed in the systems and methods herein, the brain can be reprogrammed/recalibrated to process the information correctly in a very short time frame—months and not years. Thus, the systems and methods herein implement corrective processes that provide a reliable and facile way to diagnose and treat dyslexia (and other reading disabilities). While the study of reading disorders have been classified under a branch of psychology, the systems and methods herein correct reading disorders via a vision approach. Stated another way, the reading disorder is treated as a vision problem that should be treated by an eye care professional that is corrected via the systems and methods herein. While psychologists attempt to solve dyslexia by treating it as an auditory based problem, the systems and methods herein are correcting visual processing problem and not using auditory cues. Eye doctors and psychologists are not properly educated/trained to manage dyslexia. In contrast to existing treatment for reading disorders, which are laborious and takes years for remediation, the systems and methods herein complete correction of reading disorders in about 3 months. Eye doctors and psychologists can therefore apply the systems and methods herein for the correction of reading disorders.

The systems and methods herein for correcting reading difficulties, such as dyslexia, use a series of drills, as implemented by server 125 (see FIG. 1), that emphasize key visual patterns in words via a digital alphabet. In an embodiment of the systems and methods herein, a computing environment is to provide digital alphabet comprising five buckets of pieces (Bucket 1, Bucket 2, Bucket 3, Bucket 4, and Bucket 5). Bucket 1 is a set of short anchor pieces, which are 2-digit letters; Bucket 2 is a set of long anchor pieces, which are 3-digit letters; Bucket 3 is a set of double vowel pieces; Bucket 4 is a set of beginning pieces (prefixes), which vary in length; and Bucket 5 is set of ending pieces (suffixes), which vary in length. The server 125 can be connected to device 105 via network 120 (i.e., a telecommunications network). Device 105 can be a smartphone, laptop, desktop, tablet, or any programmable device.

Bucket 1, Bucket 2, Bucket 3, Bucket 4, and Bucket 5 can be provided to the patients in digital form as tables/matrices (see FIGS. 3A, 3B, 3C, 4A, 4B, 4C, 4D, 4E, 4F, 4G, 4H, 4I, 4J, and 4K). Also, enclosed is a propriety test called the Visual Pattern Recognition Test which has been used for diagnostic purposes, but never given out to patients.

The server 125, which is run by a doctor, therapist, or parent, can administer the drills on a program 115 in use by the patient on device 105. The program 115 can be equipped with video and audio modules residing within the program 115 or managed by server 125 via the program 115 and optometric equipment, which is managed by the server 125. This allows the server 125 to extract visual and audio responses of the patients that are performing drills.

The patients are thereby identifying words quickly on graphical user interface 110 by showing them how to process words in specific fragments, which are the anchors. Essentially, poor readers learn better word identification by utilizing the alphabet in a digital and new form. While students are normally taught 26 letters and 26 sounds, actual reading does not work that way. Just like when counting, there are single digit numbers, double digit numbers, and triple digit numbers, and so forth. The server 125 is administering drills that teach patients about double digit letters, triple digit letters, and quadruple digit letters patterns. Once the patients recognize that words are structured in these fragments and learn how to sequence the fragments in the proper order, patients can read the words in seconds without sounding out the words. This concept is visual pattern recognition (see FIG. 3D). In regular reading, the patient is told to sound out the words. In contrast, the server 125 of the systems and methods herein is prompting the student to tell the server 125 what the patients see. All the sounds of these anchors are already known. Thus, the patient does not need to learn any new sounds. In the training process of the drills, the patient discovers that he or she knows the sounds by giving them familiar words that have those sounds as a clue, as provided by the server 125. Thereby, the patient is getting reprogrammed by referencing words they already know or have spoken by honing in on visual pattern recognition as opposed to auditory pattern recognition. This is counterintuitive to traditional techniques in enhancing word recognition.

Another factor related to this is that dyslexic patients actually see the wrong thing until they are asked. In fact, most dyslexic patients identify a word incorrectly and insert letters that are not even there. Their mind tells them that the words is different than what it actually is, almost like an illusion. Some dyslexic patient reverse and jumble letters, while other dyslexic patients do not. However, just about all of dyslexic patients see things that are not there. The drills, as provided by the server 125, teach the patients how to assemble and disassemble the words within the graphical user interface 100 and is akin to using the anchors as letter "bricks". The builder sees the bricks and builds the structures as shown in the drawings and not necessarily as written instruction. The server 125 of the systems and methods herein provides drills in which the anchors create 'bricks' for correcting reading dyslexia and other reading deficiencies and the word structure. The bricks are therefore letter tiles composed of the anchors.

The server 125 also administers drills that teach the patient how to track words in the right order. The combination of server 125 and drills (e.g., the tiles disclosed herein) of the corrective systems and methods herein enhance visual pattern recognition and mental stamina. Ninety five percent of those with reading disabilities and learning disabilities have tracking problems. Using special tracking drills, computer software (the video and audio modules residing within program 115 or managed by server 125 via the program 115) and optometric equipment (managed by the server 125), the server 125 is teaching the patients to track the words properly and efficiently due to the enhanced visual pattern recognition and mental stamina. When tracking occurs effortlessly, the brain can process the content faster and with less confusion. For example, most dyslexic patients are smart intellectually, have large speaking vocabulary, and good oral comprehension, but display poor word recognition, slow reading speed, and poor reading comprehension. While traditional methods ask patients to "sound out the words", the corrective systems and methods herein ask the patients to "tell the administrator what he or she is seeing", which allows the administrator to determine if the patient is seeing words or parts of words that are actually there, thereby eliminating words or parts of words that are falsely inserted, omitted, or transposed by the reader. Stated another way, reader can recognize visual errors associated the words or parts of words that are falsely inserted, omitted, or transposed (i.e., imaginary words or parts of words), thereby the reader eliminates the falsely inserted words or parts of wards. This is the basis for fixing word recognition and tracking. By fixing word recognition and tracking by the corrective systems and methods herein, reading performances of patients can jump grades ahead in record time. Patients can read with better fluency, speed, and comprehension with proficiency at least equivalent to their spoken vocabulary level. The word recognition process lets patients identify and properly pronounce 90% of the English language, even if the patient has never seen the word before. This also improves spelling.

Special letter tiles made using digitized combinations. The tiles are made to fit together in certain order and direction. An added feature is to place the tiles into a track to provide some audio component for those that need the extra help.

In one embodiment, building bricks may be made as a plastic "sleeve or box" with a window for a word fragment/ anchor. Each brick may have all the anchors of certain type encased allowing a specific anchor to be scrolled as needed to the window. This way, 500 individual bricks would not be required. Instead, only 5 bricks for the 5 categories of pieces may be used. The individual bricks may have a printed display with ink or a digital LED display. In one embodiment, a verbal piece may be used with an audio chip. Training and learning concepts remain the same while different tools may be used for the same function related to word recognition skills.

In one embodiment, for applying word recognition skills using the multiple digit letter concept, instead of just having printed letter tiles (like scrabble tiles) with categories of the short anchors (i.e., double-digit letters), long anchors (i.e., triple-digit letters), double vowel anchors (double digit), pre-fix anchors (2-3 letters), and suffix anchors (2-5 letters), which amount to about 475 different tiles, only 6 tile pieces may be used. The tiles may be implemented in an electronic format which has an LCD display that could show any characters that fit in a particular anchor bucket with the sixth electronic tiles designated for single digit letters. In other words, one electronic tile may store all the short anchors, another electronic tile would store all the long anchors, and so on. Also, the tiles could connect and plug into each other or into a track that would have a verbal output to check pronunciation accuracy. It may also have a built-in error tone or light to signal that component tiles are not assembled in the correct order or sequence.

As another embodiment, a plastic or paper slide conversion chart, which is made up of sleeve with a window to show different letter combinations printed on cards that can be slipped into the sleeve and show a word through the window may be used. This implementation would have more than six tiles, but less than 475 tiles. Thus, the recognition skills using the multiple digit letter concept may employ a tool with as few pieces as possible, but the use and the application of the concept is the same as described herein.

According to the exemplary embodiments, word recognition is used as teaching approach using visual patterns. The reader is asked what they see. Conventional sound patterns are not emphasized, because they are already in the reader's head, because they have been speaking since the age of 2 or earlier. Emphasis is placed on letter combinations and their relative positions in the words (i.e., patterns).

Words are broken into fragments called anchors which are equivalent to digital building bricks of single digit letters, double digit letters, triple digit letters, quadruple digit letter, and some quintuple combinations. Word anchors are smaller fragments than syllables and are much more consistent and accurate for pronunciation of words. When words are broken and spoken by word anchors, the words pair well with the readers oral library of words.

According to the exemplary embodiments, by identifying, localizing, and sequencing word anchors in a specific order, any reader can consistently pronounce known and unknown words. With unfamiliar words, the reader needs to follow a certain order of operations which is not performed left to right, but right to left. The reader also needs to start with the anchors. Various drills are used to break bad brain habits. The exemplary method has a high level of consistency and very few rules to remember.

The server 125 can also implement computer software module in the program 115 specifically designed to improve the tracking ability (e.g., generating scores over time for a patient to assess his or her progress in correcting reading problems in response to performing the drills).

The server 125 can also print a workbook with words showing pictures of the process without using written instructions (e.g., words are broken down into component parts by color or spacing), which is similar to a Lego brick instruction. There may be supplementary component using special colored or polarized filters placed over special cards to show how to break words up by anchors (i.e., another visual type cue to help process the words).

Figure 2:
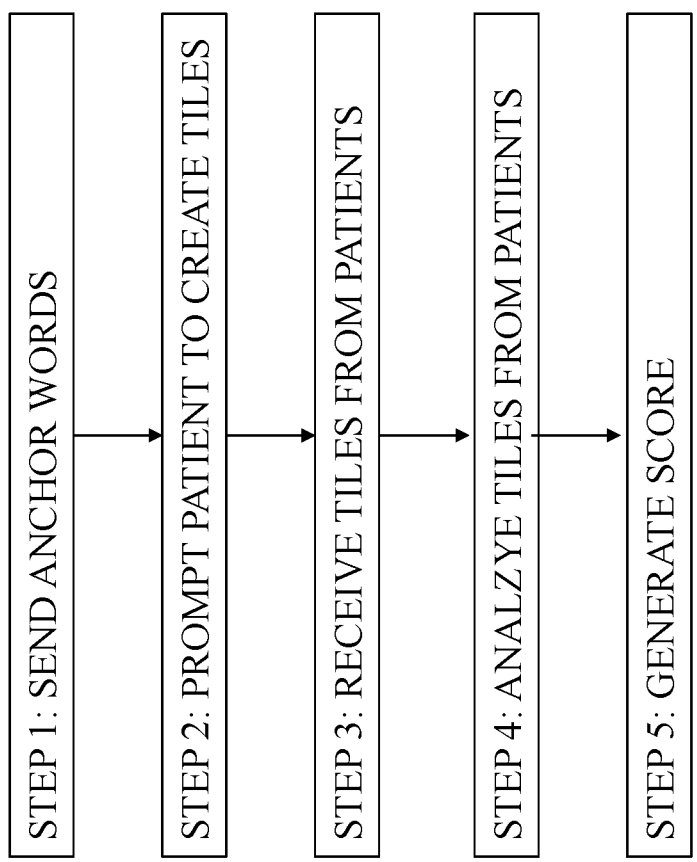
FIG. 2 is a depiction of a flowchart that utilizes the computing environment for dyslexia and correcting reading deficiencies.

The server 125 can implement steps 1-5 of the flowchart depicted in FIG. 2. For example, the server 125 sends anchor words to program 115, which are displayed on user interface 110 on device 105 (in step 1); prompt the patient using program 115 to create tiles (in step 2); receive the tiles and associated responses from patients (in step 3); analyze the tiles and associated responses from the patients (in step 4);

and generate a score which assesses the progress over time in correcting Dyslexia and other reading deficiencies (in step 5).

The anchors are sent as short or long anchors matrixes, prefixes, suffixes, and double vowel pieces, where: Bucket 1 is a set of short anchor pieces, which are 2-digit letters; Bucket 2 is a set of long anchor pieces, which are 3-digit letters; Bucket 3 is a set of double vowel pieces; Bucket 4 is a set of beginning pieces (prefixes), which vary in length; and Bucket 5 is set of ending pieces (suffixes), which vary in length. (See FIGS. 3A, 3B, and 3C.)

The steps of the flowchart can be used for testing purposes and treatment directed to correcting Dyslexia and other reading deficiencies. When the patient in prompted in step 2 by the server 125, instructions within the drills include: having the patient read each bold print letter group; showing one line at a time when showing letter groups; blocking words in the row directly below letter groups. The responses to the instructions (i.e., the tiles and associated response received from patients in step 3) are analyzed as to highlight any correct response and not highlight incorrect responses. For any incorrect responses, the server 125 reverts to step 2 and thereby prompting the patient to read the word underneath the letter groups missed. If the patient is determined to be able to read the word by the server 125, then server 125 reverts to step 2 and thereby prompting the patient to re-read the letter group in bold print above it. Correct responses on the bold print groups are highlighted in a second color, as analyzed by the server 125. The responses are scored over time by counting the number correct response of groups (alone), groups (by context), and misses. In one example, short anchors are shown in rows 1-5, long anchors are shown in rows 6-8, double vowels are shown in row 9, and prefix blends are shown in row 10 of the user interface 110. The server 125 can apply the visual pattern recognition test to determine if the responses are correct.

Figure 4A:
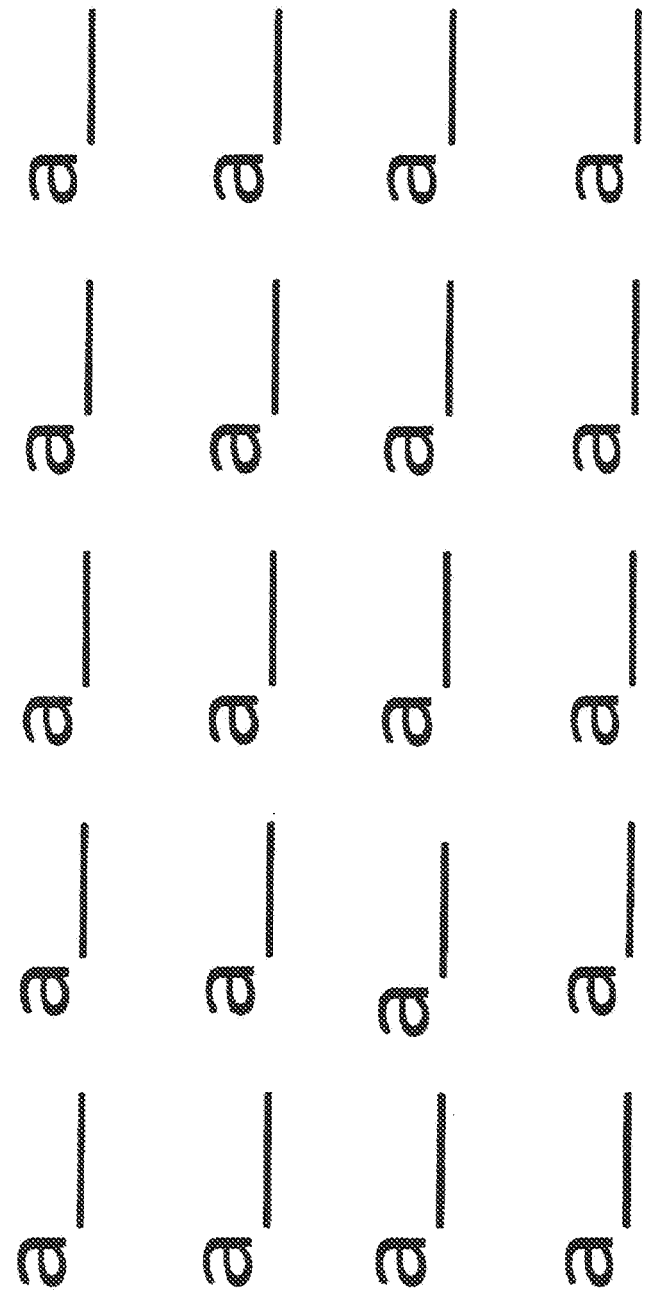
Figure 4E:
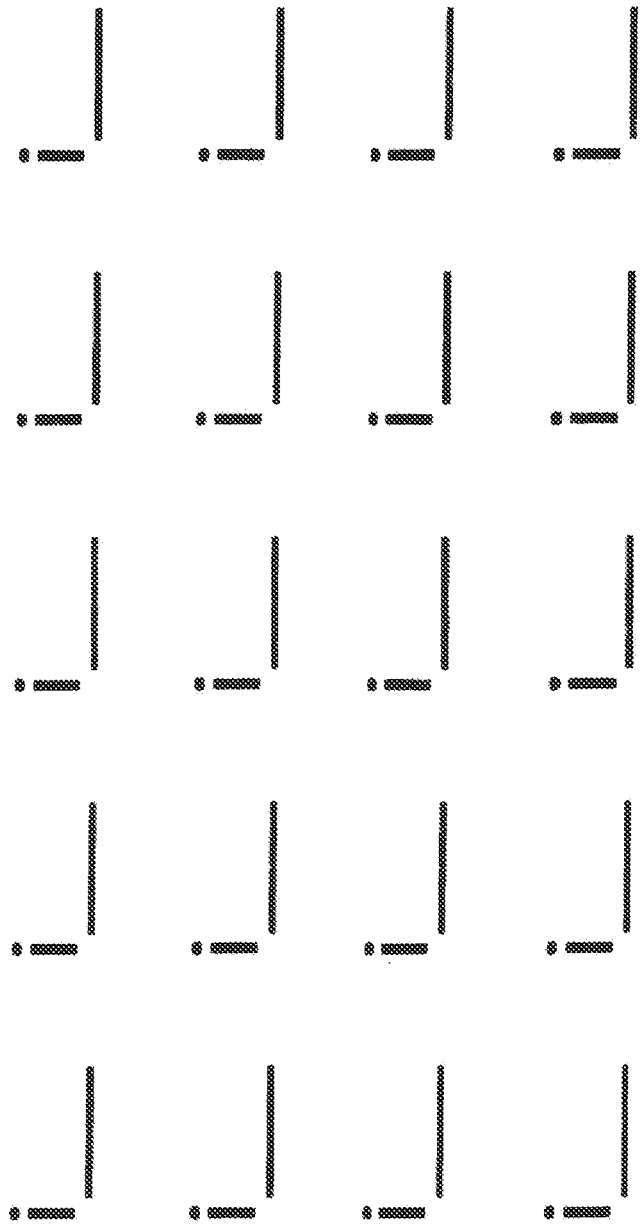
Figure 4G:
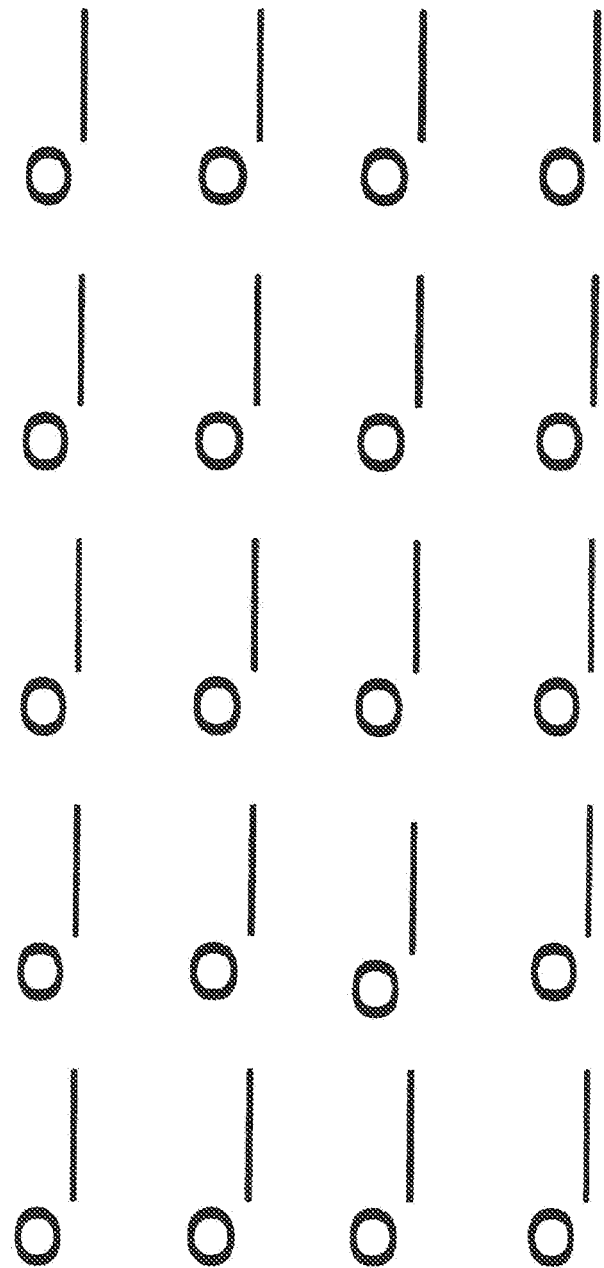
Figure 4I:
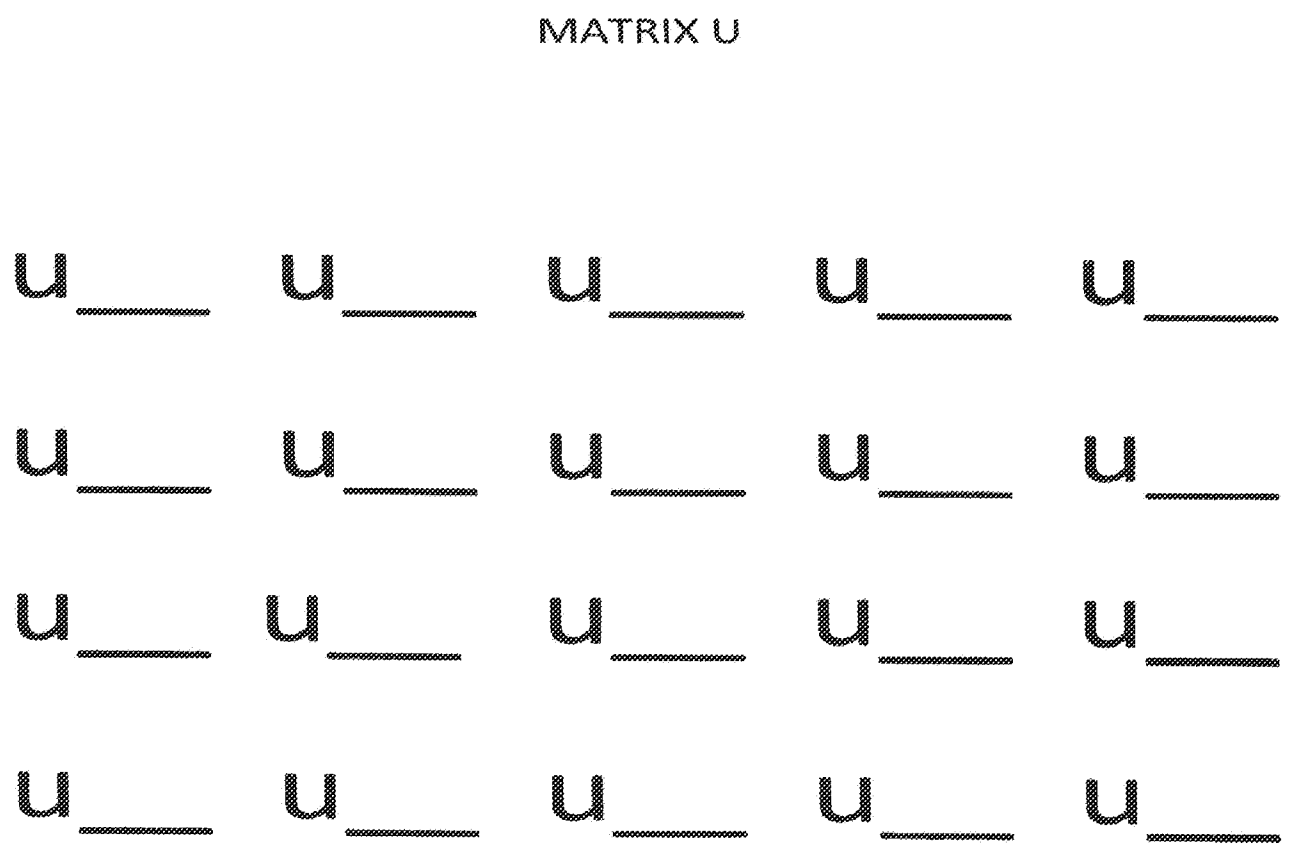
Figure 4K:
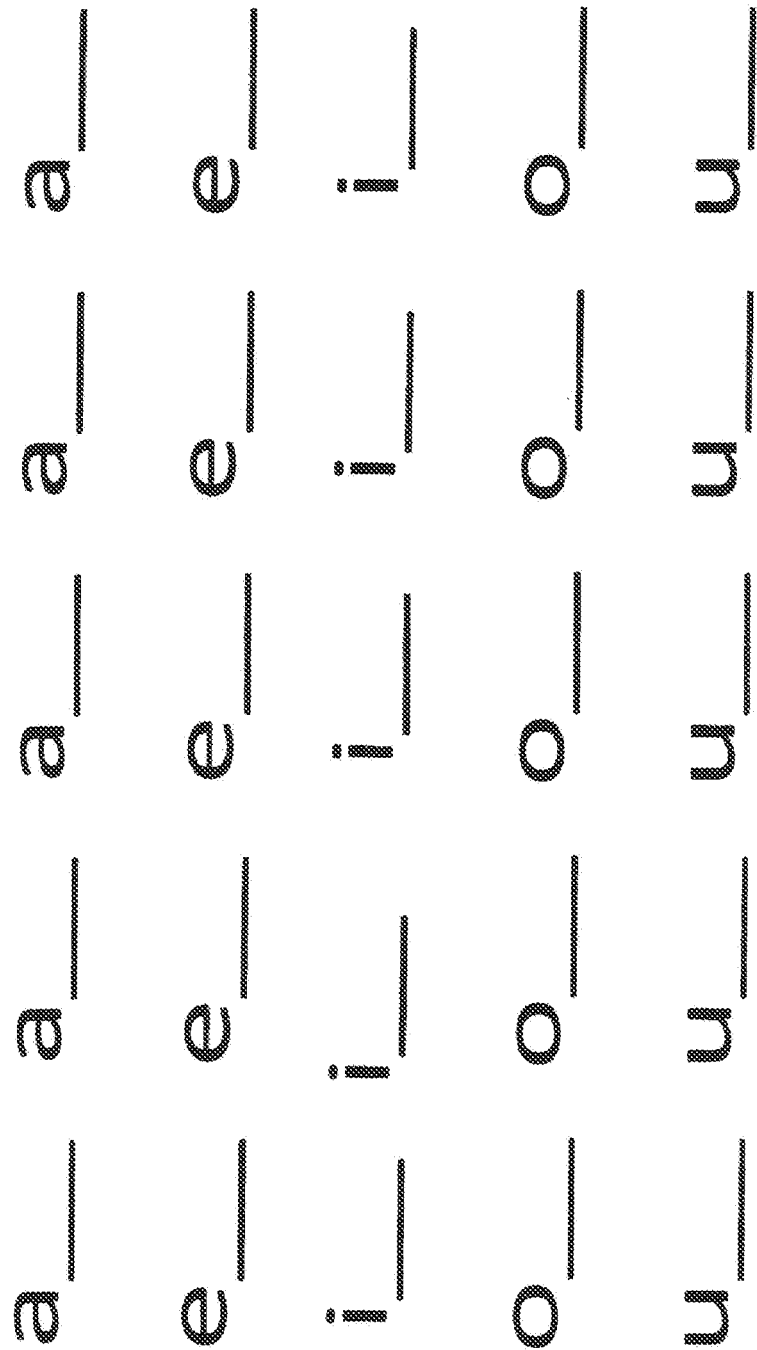

The server 125 can send the following to program 115, which are subsequently analyzed: matrix A (which corresponds to C1 in FIG. 3A) of FIG. 4A and power E matrix (which corresponds to C6 in FIG. 3A) of FIG. 4B; matrix E (which corresponds to C2 in FIG. 3A) of FIG. 4C and power E matrix (which corresponds to C7 in FIG. 3A) of FIG. 4D; matrix I (which corresponds to C3 in FIG. 3A) of FIG. 4E and power E matrix (which corresponds to C8 in FIG. 3A) of FIG. 4F; matrix O (which corresponds to C4 in FIG. 3A) of FIG. 4G and power E matrix (which corresponds to C9 in FIG. 3A) of FIG. 4H; matrix U (which corresponds to C5 in FIG. 3A) of FIG. 4I and power E matrix (which corresponds to C10 in FIG. 3A) of FIG. 4J; matrix double vowel of FIG. 4K.

The drills, as administered by the server 125, can involve pattern recognition drills and reading neuro-motor drills. An example of a drill administered and processed by the server 125 is depicted in FIG. 5. In FIG. 5, a few word examples (bricks) are broken down by anchors (or tiles) and reassembled by sequencing in reverse order. This aids dyslexic patients that have sequencing problems with words and/or parts of words. The corrective systems and methods herein can involve building upon the anchors which builds the whole word, such as 'investigate', 'pandemonium', and 'unconsciously'. More specifically, anchors are pulled, lead letters are added to the pulled anchor, and sequence of anchors are approached from simple tiles to the whole words (e.g., "ate" to "tigate" to "vestigate" to "investigate").

Identification drills within pattern recognition drills via letter matrices, white board, letter tiles, RWL computer software (eye-trainer and Taschiscopic Flash and Recall game) comprise: 1) identifying and reviewing short and long vowels (start with short vowels and proceed to the long vowels but not in the same session); 2) identifying and reviewing key letter groups by sight, sound, and writing (not necessarily in the same session); 3) starting with short anchor groups, followed by prefix and suffix groups; 4) proceeding to long anchor groups and then double vowel groups; 5) eventually identifying simple whole words; 6) building speed of whole word recognition using Flash and Recall games with endpoint goal of 50 msec; and 7) reading whole words using eyer trainer of RWL computer software, which can be manifested as program 115. In doing these steps, the following results are achieved: key letter groups and words are quickly and accurately identified by sight and sound; the patient is re-programmed to process words uses the digital alphabet; the patient is trained to consistently look for common key letter patterns; a visual based structure is provided that does not emphasize phonics; and the patient is taught the majority of key letter groups that do not change their sound. There are some minor exceptions, but there are fewer exceptions than when using phonics-based approach. Thereby, the corrective systems and methods herein provide the patients with: (i) increased consistency and reliability when processing visual based structures and patterns; and (ii) a framework for processing more complex word structures or previously unrecognized word structures.

Other aspects of the identification drills include: words are composed of common letter sequences that do not change their sound for the majority of words; poor word recognition occurs because the patient cannot correctly identify component parts; poor readers frequently assign wrong vowels sounds (e.g., interchanging e for I or a for e); poor reader frequently change the sounds of the key letter components when provided in different sequences; the RWL software teaches patterns organized by short and long vowel sounds to create key word anchors, which are visual fragment; and visual fragments. Note that visual fragments are smaller than sound fragments (syllables) in most cases. For example, "et" is the anchor for pet, which is smaller than the syllable "pet"; and for the word "faster", "er" is the anchor and the syllable.

The patient is prompted to respond to matrices described above. This procedure involves: discuss and reviewing five vowels starting with the short sounds "a e i o u"; using letter matrices to show common letters based upon vowels; patient filling in the blanks on the letter matrices with all consonants minus q; and filling in 20 consonants horizontally or vertically. Once the matrix is completed, it represents Short Anchors (key groups with short sound). Patient reads and says letter groups using short vowel sound. Doctor/therapist, via the server 125, guides the patient thru process and corrects any wrong sounds. The patient learns short anchors until he or she can iterate without hesitation (min. goal 60/60 sec). Patient repeats process for Matrices A, E, I, O, U (can be done over multiple visits). Once the patient is familiar with Short Anchors and matrices patient moves to Long Anchors. Long Anchors are created by adding a lower case "e" to the end of all major Short Anchors. Patient needs to read and say long anchors using long sounds for a, e, i, o, u. Doctor/therapist guides patient thru process and correct any wrong sounds. Some groups in matrices are not real and are there to demonstrate the pattern of construction. In Short vs Long Matrix bold print indicates real groups. Matrices continue with double vowel matrix (which tends to be the hardest due to some blended sounds and some split sounds). Complete Matrices with Prefixes and Suffixes. Prefixes are fixed blended consonant sounds added to anchors to make syllables. Suffixes are common endings of words that have fixed sounds.

Construction drills within pattern recognition drills via letter matrices, white board, letter tiles, comprise: 1) adding the different single letters to a single short anchor group and working with long anchors at a later session; 2) adding the same single letter to different short anchors and work with anchors at a later session; 3) adding prefixes to short anchors and then long anchors (later session); 4) building double syllable words with two anchors; 5) building multiple syllable words with multiple anchors; and 6) adding suffixes and double vowels as needed. In doing these steps, the following results are achieved: the construction of words using anchors is demonstrated; words are taught to be constructed of single letter sounds and group letter sounds; words with similar spelling are recognized as to having similar sounds (rhyming); and syllables are quickly recognized using key visual anchors.

Other aspects of the construction drills include: sounding words out using single letter sounds is ineffective for word pronunciation; phonics uses sound fragments and RWL uses visual fragments; visual fragments are smaller than syllables; poor readers have difficulty processing visual fragments and auditory fragments; processing errors occurs because reading is left to right but word construction is built right to left; visual fragments are anchors because single letter or blends are added to the front of the anchor to make syllables; and traditional phonic approaches put emphasis on lead letters.

The construction drills involve Drills 1, 2, 3, and 4.

In Drill 1, have a patient write a column of any short anchor on white board (usually 10); add a single letter tile (consonants only) to first anchor creating one syllable word; have patient say one syllable word or fragment making corrections as necessary; add a different single letter (consonants only) to second anchor making a new one syllable word; keep adding a different consonants to each line making new 10 different one syllable word still emphasizing rhyming and common visual pattern; creating syllables that are not words is acceptable and will be used later for multisyllable words; do not erase column of anchors, but remove 10 letter tiles where existing columns act as reference; have patient start a new column of 10, using a different short anchor and build 10 new one syllable words; repeat process until 5 or 6 columns of anchors exists; and move to long anchors on a subsequent visit.

In Drill 2, select a single letter tile and place it in front of any anchor in any column; have patient say the one syllable word or fragment making corrections as needed; transfer same letter from column to column having patient say each one syllable word or fragment; build automaticity for syllable recognition and quick changes in processing different letter combinations; and move to long anchors after a subsequent visit.

In Drill 3, continue drills 1 and 2 but use double consonant blends from prefix list; and when successful, add triple letter blends which again emphasizing common patterns.

In Drill 4, begin demonstrating two anchors next to each other; have patient say each anchor as a separate component; have patient read each component (syllable) in sequence to form a two syllable word; once successful, move to 3 or more syllable words; emphasize not altering sounds of syllables when combining for whole word formation; and if patient fails, and re-visit drills 1 and 2 for the failed piece.

Localization and sequencing drills within pattern recognition drills via word lists, highlighters, while board, and transparency comprise: 1) finding key anchor groups in words; 2) highlighting key anchor groups; 3) starting at right and going left (this is opposite of reading); 4) using various break apart drills if necessary (horizontal or vertical); 5) using construction skills to add letters and prefixes to identify syllables; 6) identifying components and reassembling left to right; and 7) working toward just visualizing key anchors and other components. In doing these steps, the following results are achieved: key components that give word structure are localized; proper segmentation of words into syllables is taught using visual patterns; words are broken down and reassembled for proper word pronunciation; and word recognition is faster and more accurate.

Other aspects of localization and sequencing drills include: poor readers are unable to localize key letter groups; lead letters used for word recognition causes guessing and substitution; anchor which are localized lead to faster word recognition; anchors are localized starting on the right and moving to the left; consonants are assigned after finding the anchors; and one key anchor is localized, which allows identification of whole words.

In the procedure for localization and sequencing drills, choose grade level appropriate word list; begin with one syllable words and highlight with marker the key anchor and say the word; then have patient select another word and highlight the familiar key letter group(s); repeat the process until patient understands completely; proceed to a double syllable word find more than one key anchor and have patient say word; make sure the patient looks for key anchors starting on the right and move left; if highlighting is not working well, have patient write each anchor separate on the white board horizontally or vertically and add remaining consonants back to pieces as in construction drills; work toward only visualizing pieces to read whole word; practice both single and multiple syllable words using above strategies; check and review prefixes and suffixes; when practicing multiple syllable words, look for word segments within the words, for example, telephone had the word phone in it; and remove endings to assist in word identification if necessary, show root word first, for example interesting remove "ing".

Saccadic drills within reading neuro-motor drills via RWL computer software, vergence facility, accommodative facility, print material, and choice video games, comprise: 1) working span of recognition with Eye Span Game with endpoint goal of 500 msec; 2) training proper reader saccades and minimize regressions with eye-trainer 1-3 word scroll; 3) loading visual system incrementally with vergence facility using flex/hold techniques; 4) reading stories with eye trainer in auto and manual modes with and without vergence facility; 5) building speed by reading stories in eye trainer in auto and manual modes; 6) driving speed by using alternate reading techniques; 7) regression reducing change eye-trainer to two fixations and eventually whole lines and/or punctuation; 8) reading print material with and without vergence facility and accommodative facility in flex/hold drills; and 9) playing tracking video games with and without vergence facility in flex/hold drills.

The Eye-span Game (Hands on Training) is characterized by the following below.
  Location: in Menu Mode under Brain Games;
  Purpose: build span of recognition and to quickly identify adjacent text;
  Goal: achieve 500 msec for two words on same line close setting;
  Instructions: on screen; and Variables: word spacing, line spacing, number of words, speed, rest time.

The Eye Trainer (Hands on Training) is characterized by the following below:

Location: in Reading Mode;

Purpose: to train proper rhythm of forward left to right movements and remove regressions (backward movements);

Goal: oral reading and silent reading at or above grade level (max oral reading approx. 170);

Instructions: on screen; and

Variables: fonts size and colors, background colors, multiple word displays, location on screen, speed, key letter groups, library of stories grade 1-12, importing of custom word documents.

Reading Rate and Comprehension (Hands on Training) are characterized by the following below:

Location: Menu Mode;

Purpose: monitor progress of reading rate and comprehension in regular reading format;

Goal: achieve grade level or higher reading rate and 90% or better comprehension;

Instructions: on screen; and

Variables: grade level reading material.

Vergence drills within reading neuro-motor drills via incremental increases in demand by increasing prism flipper amounts RWL computer software, vergence facility, plastic frame with elastic strap, and print material, comprises: 1) vergence facility flex/relax with grade level print material or word list; 2) vergence facility flex/hold with grade level print material or word list; 3) vergence facility flex/hold with various reading drills and games in electronic format; 4) vergence facility flex/hold with word finds, video games, and drawings; and 5) supplemental vergence training with other VT techniques as needed.

The vergence facility is characterized by the following below:

Purpose: BI/BO vergence facility with prism flippers to build incremental stress and strength;

Exercises: Flex/Relax Drill for flexibility;

Goal: read 32 words or numbers from list in one minute without double vision or strain;

Work from 2-16 PD;

Flex/hold drill for stamina;

Goal: read 10 pages in 10 minutes at grade level material without double vision or strain;

Work from 2-16 PD;

Flex/Hold Combo Drills;

Purpose: improve saccadic versatility under various vergence demands;

Goal: combine vergence flex/hold with eye-trainer, eye-span, and tachiscopic flash and recall;

Technique: proper working distance and font size for book, tablet, or computer;

Use pl/BI or pl/BO if required;

Blinking as needed to facilitate sustained fusion;

Small in/out movements to facilitate sustained fusion; and

Taking breaks as needed.

Accommodation drills within reading neuro-motor drills via incremental increases in demand by increasing prism flipper amounts RWL computer software, vergence facility, plastic frame with elastic strap, and print material, comprises: 1) tachiscopic flash and recall game on program 115 or a DVD; 2) accommodative facility flex/relax with grade level print material or word list; 3) accommodative facility flex/hold with grade level print material or word list; 4) accommodative facility flex/hold with various reading drills and games in electronic format; 5) accommodative facility flex/hold with word finds, video games, and drawings; and 6) supplemental accommodation training with other VT techniques as needed.

Accommodation drills are characterized by the following:

Purpose: +/− facility with lens flippers to build incremental stress and strength;

Exercises: Flex/Relax Drill for flexibility;

Goal: read 32 words or numbers from list in one minute without blurred vision or strain;

Work from 0.50-2.00 D;

Flex/Hold Drill for stamina;

Goal: read 10 pages in 10 minutes at grade level material without blurred vision or strain;

Work from 0.50-2.00 D;

Flex/Hold Combo Drills;

Purpose: improve saccadic versatility under various accommodative demands;

Goal: combine accommodative flex/hold with eye-trainer, eye-span, and flash and recall;

Technique: proper working distance and font size for book, tablet, or computer Use pl/+ or PI/− if required;

Blinking as needed to facilitate sustained focus;

Small in/out movements to facilitate sustained focus;

Taking breaks as needed;

Flex/Relax: alternating sides of flipper within a short period; and

Flex/Hold: alternating sides of flipper and holding each side for extended periods flip every line, flip by 2 lines, flip by 3 lines, work up to paragraph or page.

The nodes in computing environment of FIG. 1 are computer system/server which are on the form of a general-purpose computing device. The components of computer system/server may include, but are not limited to, one or more processors or processing units, a system memory, and a bus that couples various system components including system memory to processor.

Bus represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server typically includes a variety of computer system readable media. Such media may be any available media that is accessible by a computer system/server, and it includes both volatile and non-volatile media, removable and non-removable media.

System memory can include computer system readable media in the form of volatile memory, such as random access memory (RAM) and/or cache memory. Computer system/server may further include other removable/nonremovable, volatile/non-volatile computer system storage media. By way of example only, storage system can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to a bus by one or more data media interfaces. As will be further depicted and described below, the memory may include at least one program product having a set (e.g., at least one) of program modules that are configured to carry out the functions of embodiments of the invention.

Program/utility, having a set (at least one) of program modules, may be stored in memory by way of example, and not limitation, as well as an operating system, one or more application programs, other program modules, and program data. Each of the operating system, one or more application programs, other program modules, and program data or some combination thereof, may include an implementation of a networking environment. Program modules generally carry out the functions and/or methodologies of embodiments of the invention as described herein.

Computer system/server may also communicate with one or more external devices, such as a keyboard, a pointing device, a display, etc.; one or more devices that enable a user to interact with a computer system/server; and/or any devices (e.g., network card, modem, etc.) that enable computer system/server to communicate with one or more other computing devices. Such communication can occur via Input/Output (I/O) interfaces. Still yet, computer system/server can communicate with one or more networks such as a local area network (LAN), a general wide area network (WAN), and/or a public network (e.g., the Internet) via network adapter. A network adapter communicates with the other components of computer system/server via the bus. It should be understood that although not shown, other hardware and/or software components could be used in conjunction with computer system/server. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is:

1. A system for correcting dyslexia and reading deficiencies, comprising:
    a processor of a server connected to a user device running a dyslexia treatment application over a network;
    a memory on which are stored machine-readable instructions that when executed by the processor, cause the processor to:
        send a plurality of anchor words to the user device to be displayed on a user interface of the dyslexia treatment application wherein the plurality of anchors is sent as a digital alphabet comprising five buckets of pieces comprising:
            bucket 1 comprising a set of short anchor pieces made of 2-digit letters;
            bucket 2 comprising a set of long anchor pieces made of 3-digit letters;
            bucket 3 comprising a set of double vowel pieces;
            bucket 4 comprising a set of beginning pieces made of prefixes varying in length; and
            bucket 5 comprising set of ending pieces made of suffixes varying in length;
        provide at least one prompt to the user of the dyslexia treatment application to create tiles based on the plurality of the anchor words;
        responsive to receiving the tiles and associated responses from the user of the dyslexia treatment application, analyze the tiles and the associated responses; and
        generate a score based on analysis of the tiles and the associated responses.

2. The system of claim 1, wherein the instructions further cause the processor to assess progress over time in correcting dyslexia and other reading deficiencies based on the score.

3. The system of claim 1, wherein:
    the short anchor pieces are provided as short anchor matrices;
    the long anchor pieces are provided as long anchor matrices;
    the double vowel pieces are provided as double vowel matrices.

4. The system of claim 1, wherein the server is configured to receive audio and video data from the dyslexia treatment application.

5. The system of claim 4, wherein the instructions further cause the processor to administer drills to the user via the dyslexia treatment application that teach the user about double digit letters, triple digit letters, and quadruple digit letters patterns based on visual pattern recognition.

6. The system of claim 1, wherein the instructions further cause the processor to extract visual and audio responses from the dyslexia treatment application to perform the analysis.

7. A method for correcting dyslexia and reading deficiencies, comprising:
    sending, by a server, a plurality of anchor words to a user device to be displayed on a user interface of the dyslexia treatment application, wherein the plurality of anchors is sent as a digital alphabet comprising five buckets of pieces comprising:
        bucket 1 comprising a set of short anchor pieces made of 2-digit letters;
        bucket 2 comprising a set of long anchor pieces made of 3-digit letters;
        bucket 3 comprising a set of double vowel pieces;
        bucket 4 comprising a set of beginning pieces made of prefixes varying in length; and
        bucket 5 comprising set of ending pieces made of suffixes varying in length;
    providing, by the server, at least one prompt to the user of the dyslexia treatment application to create tiles based on the plurality of the anchor words;
    responsive to receiving the tiles and associated responses from the user of the dyslexia treatment application, analyzing, by the server, the tiles and the associated responses; and
    generating, by the server, a score based on analysis of the tiles and the associated responses.

8. The method of claim 7, further comprising assessing progress over time in correcting dyslexia and other reading deficiencies based on the score.

9. The method of claim 7, sending the plurality of anchors comprising any of: short anchors matrixes, long anchor matrixes, prefixes, suffixes, and double vowel pieces.

10. The method of claim 7, further comprising receiving audio and video data from the dyslexia treatment application.

11. The method of claim 10, further comprising extracting visual and audio responses from the dyslexia treatment application to perform the analysis.

12. The method of claim 7, further comprising administering drills to the user via the dyslexia treatment application that teach the user about double digit letters, triple digit letters, and quadruple digit letters patterns based on visual pattern recognition.

13. The method of claim 7, further comprising administering at least one drill to the user via the dyslexia treatment application, the drill comprising:
- an identification drill to teach the user to identify and read the anchor words;
- a pattern identification drill to identify the anchor words within whole words and to extract the anchor words from the whole words, and reassembling the word using the extracted anchor;
- a construction drill to teach the user to construct syllables by adding a consonant to at least some of the anchor words and by putting the constructed syllables together;
- a saccadic drill to build up speed in reading by training the user to read forward left to right eye movement, while reducing regression of the eye, and by building incremental stress and strength of the user's eye.

14. A method for correcting dyslexia and reading deficiencies, comprising:
- providing a plurality of anchor words to a user, the anchor words comprising: a set of anchor pieces starting with vowels, a set of beginning pieces, and a set of ending pieces;
- providing at least one prompt to the user to create tiles based on the plurality of the anchor words;
- responsive to receiving the tiles and associated responses from the user, analyzing, the tiles and the associated responses; and
- scoring, based on analysis of the tiles and the associated responses,
- wherein providing a plurality of anchor words to a user comprises providing physical building bricks, each made as a "sleeve or box" with a window for the anchor word, each brick having all the anchors of certain type encased so as to allow a specific anchor to be scrolled as needed to the window.

15. The method of claim 14, wherein the anchor pieces comprise at least one of:
- a set of short anchor pieces made of two letters;
- a set of long anchor pieces made of three letters;
- a set of double vowel pieces.

16. The method of claim 14, wherein:
- each of the short anchor pieces is formed by a vowel followed by a consonant;
- each of the long anchor pieces is formed by a vowel followed by a consonant followed by a vowel;
- each of the double vowel pieces is formed by a vowel followed by a vowel.

17. The method of claim 14, further comprising administering at least one drill comprising at least one of:
- an identification drill to teach the user to identify and read the anchor words;
- a pattern identification drill to identify the anchor words within whole words and to extract the anchor words from the whole words, and reassembling the word using the extracted anchor;
- a construction drill to teach the user to construct syllables by adding a consonant to at least some of the anchor words and by putting the constructed syllables together;
- a saccadic drill to build up speed in reading by training the user to read forward left to right eye movement, while reducing regression of the eye, and by building incremental stress and strength of the user's eye.

18. The method of claim 14, wherein each of physical building bricks has the window showing a printed display with ink or a digital LED display having all the anchors of certain type so as to allow a specific anchor to be scrolled as needed to the window.

* * * * *